United States Patent [19]

Onda et al.

[11] Patent Number: 5,756,344
[45] Date of Patent: May 26, 1998

[54] DNA CODING FOR A HUMAN VASOCONSTRICTIVE PEPTIDE AND USE THEREOF

[75] Inventors: Haruo Onda; Shoichi Ohkubo; Takuo Kosaka, all of Tsukuba Ibaraki, Japan

[73] Assignee: Takeda Chemical Industries, Ltd.

[21] Appl. No.: 673,269

[22] Filed: Jun. 28, 1996

Related U.S. Application Data

[63] Continuation of Ser. No. 728,169, Jul. 10, 1991.

[30] Foreign Application Priority Data

Jul. 18, 1990 [JP] Japan .............................. 187960/1990
Jan. 10, 1991 [JP] Japan .............................. 001451/1991
Jun. 14, 1991 [JP] Japan .............................. 143127/1991

[51] Int. Cl.$^6$ ...................... C07K 14/575; C12N 15/16; C12N 1/21
[52] U.S. Cl. .................. 435/252.3; 435/69.4; 435/325; 435/252.33; 435/320.1; 530/324; 530/315; 536/23.51
[58] Field of Search ...................... 530/324, 315; 536/23.51; 435/69.4, 240.2, 252.3, 252.33, 320.1, 325

[56] References Cited

FOREIGN PATENT DOCUMENTS 315 118  5/1989  European Pat. Off. .
366016   5/1990  European Pat. Off. .

OTHER PUBLICATIONS

Yangisawa et al., "The Human Endothelin Family: cDNA Cloning, Complete Primary Structure and Differential Tissue Expression of the Three Precursors", European Journal of Pharmacology, 183(5), 1628–1629, Jul. 1990.

Yangisawa et al., "cDna Cloning and Differential Tissue Expression of Human Endothelin–2 and Endothelin–3", Japanese Journal of Pharmacology, 52, Supplement I 112P, Abstract 0–123, Mar. 1990.

Berger et al. (editors), Guide to Molecular Cloning Techniques, Methods in Enzymology, 152: 393–399, 415–423, 433–447, 661–704, 1987.

Berger, et al. (editors), Guide to Molecular Cloning Techniques, Methods in Enzymology, vol. 152, pp. 393–399, 415–423, 433–447 and 661–704, 1987.

Yangisawa et al., "cDNA Cloning and Differential Tissue Expression of Human Endothelin–2 and Endothelin–3", Japanese Journal of Pharmacology, vol. 52, Supplement I, p. 112P, Abstract 0–123, Mar. 1990.

Yangisawa et al., "The Human Endothelin Family: cDNA Cloning, Complete Primary Structure and Differential Tissue Expression of the Three Precursors", European Journal of Pharmacology, vol. 183(5), pp. 1628–1629, Jul. 1990.

Inoue et al., "The Human Endothelin Family: Three Structurally and Pharmacologically Distinct Isopeptides Predicted By Three Separate Genes", Proc. Natl. Acad. Sci., vol. 86, pp. 2863–2867, Apr. 1989.

S. Ohkubo, et al. FEBS Letters, Vo. 274, No. 1–2, Nov. 12, 1990, Amsterdam NL pp. 136–140.

Y. Itoh, et al., FEBS Letters, 231:440–444. (1988).

K.D. Bloch, et al. Genomics, vol. 10, No. 1, May 1991, San Diego, US pp. 236–242.

Primary Examiner—Rebecca E. Prouty
Attorney, Agent, or Firm—David G. Conlin; David S. Resnick; Dike, Bronstein Roberts & Cushman, LLP

[57] ABSTRACT

Disclosed are (1) a DNA containing a cDNA segment coding for human endothelin-2 (SEQ ID NO:1), (2) a precursor of human endothelin-2 (SEQ ID NO:2), (3) a transformant carrying a DNA containing a cDNA segment coding for human endothelin-2, and (4) a method for preparing mature human endothelin-2 which comprises culturing the transformant described in (3), accumulating a protein in a culture medium, and collecting the same, whereby human endothelin-2 and the precursors thereof can be produced in large amounts.

3 Claims, 9 Drawing Sheets

FIG. 1 endothelin-1

Cys Ser Cys Ser Ser Leu Met Asp Lys Glu Cys Val Tyr Phe Cys His Leu Asp Ile Ile Trp endothelin-2

Cys Ser Cys Ser Ser <u>Trp</u> <u>Leu</u> Asp Lys Glu Cys Val Tyr Phe Cys His Leu Asp Ile Ile Trp endothelin B Cys Ser Cys <u>Asn</u> Ser <u>Trp</u> <u>Leu</u> Asp Lys Glu Cys Val Tyr Phe Cys His Leu Asp Ile Ile Trp endothelin-3

Cys <u>Thr</u> Cys <u>Phe</u> <u>Thr</u> <u>Tyr</u> <u>Lys</u> Asp Lys Glu Cys Val Tyr <u>Tyr</u> Cys His Leu Asp Ile Ile Trp

FIG. 3A

```
 1      A GGA CGC TGG CAA CAG GCA CTC CCT GCT          28

29     CCA GTC CAG CCT GCG CGC TCC ACC GCC GCT         58

59     ATG GTC TCC GTG CCT ACC ACC TGG TGC TCC         88
 1      M   V   S   V   P   T   T   W   C   S         10

89     GTT GCG CTA GCC CTG CTC GTG GCC CTG CAT        118
11      V   A   L   A   L   L   V   A   L   H         20

119    GAA GGG AAG GGC CAG GCT GCT GCC ACC CTG        148
21      E   G   K   G   Q   A   A   A   T   L         30

149    GAG CAG CCA GCG TCC TCA TCT CAT GCC CAA        178
31      E   Q   P   A   S   S   S   H   A   Q         40

179    GGC ACC CAC CTT CGG CTT CGC CGT TGC TCC        208
41      G   T   H   L   R   L   R   R   C   S         50

209    TGC AGC TCC TGG CTC GAC AAG GAG TGC GTC        238
51      C   S   S   W   L   D   K   E   C   V         60

239    TAC TTC TGC CAC TTG GAC ATC ATC TGG GTG        268
61      Y   F   C   H   L   D   I   I   W   V         70

269    AAC ACT CCT GAA CAG ACA GCT CCT TAC GGC        298
71      N   T   P   E   Q   T   A   P   Y   G         80

299    CTG GGA AAC CCG CCA AGA CGC CGG CGC CGC        328
81      L   G   N   P   P   R   R   R   R   R         90

329    TCC CTG CCA AGG CGC TGT CAG TGC TCC AGT        358
91      S   L   P   R   R   C   Q   C   S   S        100

359    GCC AGG GAC CCC GCC TGT GCC ACC TTC TGC        388
101     A   R   D   P   A   C   A   T   F   C        110
```

FIG. 3B

```
389    CTT CGA AGG CCC TGG ACT GAA GCC GGG GCA    418
111     L   R   R   P   W   T   E   A   G   A     120

419    GTC CCA AGC CGG AAG TCC CCT GCA GAC GTG    448
121     V   P   S   R   K   S   P   A   D   V     130

449    TTC CAG ACT GGC AAG ACA GGG GCC ACT ACA    478
131     F   Q   T   G   K   T   G   A   T   T     140

479    GGA GAG CTT CTC CAA AGG CTG AGG GAC ATT    508
141     G   E   L   L   Q   R   L   R   D   I     150

509    TCC ACA GTC AAG AGC CTC TTT GCC AAG CGA    538
151     S   T   V   K   S   L   F   A   K   R     160

539    CAA CAG GAG GCC ATG CGG GAG CCT CGG TCC    568
161     Q   Q   E   A   M   R   E   P   R   S     170

569    ACA CAT TCC AGG TGG AGG AAG AGA TAG TGT    598
171     T   H   S   R   W   R   K   R   *         179

599    CGT GAG CTG GAG GAA CAT TGG GAA GGA AGC    628

629    GCG CGG GGA GAG AGG AGG AGA GAA GTG GCC    658

659    AGG GCT TGT GGA CTC TCT GCC TGC TTC CTG    688

689    GAC CGG GGC CTT GGT CCC AGA CAG CTG GAC    718

719    CCA TTT GCC AGG ATT GGC ACA AGC TCC CTG    748

749    GTG AGG GAG CCT CGT CCA AGG CAG TTC TGT    778

779    GTC CTC GCA CTG CCC AGG GAA GCC CTC GGC    808

809    CTC CAG ACT GCG GAG CAG CCT CCA GTG CTG    838
```

FIG. 3C

```
 839   GCT GCT GGC CCA CAG CTC TGC TGG AAG AAC    868
 869   TGC ATG GGG AGT ACA TTC ATC TGG AGG CTG    898
 899   CGT CCT GAG GAG TGT CCT GTC TGC TGG GCT    928
 929   ACA AAC CAG GAG CAA CCG TGC AGC CAC GAA    958
 959   CAC GCA TGC CTC AGC CAG CCC TGG AGA CTG    988
 989   GAT GGC TCC CCT GAG GCT GGC ATC CTG GCT   1018
1019   GGC TGT GTC CTC TCC AGC TTT CCC TCC CCA   1048
1049   GAG TTC TTG CAC CCT CAT TCC CTC GGG ACC   1078
1079   CTC CCA GTG AGA AGG GCC TGC TCT GCT TTT   1108
1109   CCT GTC TGT ATA TAA CTT ATT TGC CCT AAG   1138
1139   AAC TTT GAG AAT CCC AAT TAT TTA TTT TAA   1168
1169   TGT ATT TTT TAG ACC CTC TAT TTA CCT GCG   1198
1199   AAC TTG TGT TTA TAA TAA AT                1218
```

FIG. 4

```
                    10                  20                  30                  40                  50                  60
N-MVSVPTTWCSVALALLVALHEGKGQAAATLEQPASSSHAQGTHLRLRRCSCSSWLDKECV 70                  80                  90                 100                 110                 120
YFCHLDIIWVNTPEQTAPYGLGNPPRRRRSLPRRCQCSSARDPACATFCLRRPWTEAGA 130                 140                 150                 160                 170
VPSRKSPADVFQTGKTGATTGELLQRLRDISTVKSLFAKRQQEAMREPRSTHSRWRKR*  -C
```

DNA CODING FOR A HUMAN VASOCONSTRICTIVE PEPTIDE AND USE THEREOF

This is a continuation of application Ser. No. 07/728,169 filed on Jul. 10, 1991 pending.

FIELD OF THE INVENTION

The present invention relates to a DNA containing a cDNA segment coding for a human vasoconstrictive peptide (SEQ ID NO:1), namely human endothein-2, a precursor protein of human endothelin-2 (SEQ ID NO:2) and a method for preparing endothelin-2.

In this specification, the term "precursor protein" is preferably used to describe a protein which includes an amino acid sequence of a mature peptide and has a portion or all of an amino acid sequence coded with a DNA segment of the peptide at the N-terminus, the C-terminus or both termini thereof.

BACKGROUND OF THE INVENTION

There have been reports of endothelium-dependent vasoconstrictor reactions to various mechanical and chemical stimuli as well as endothelium-dependent vasodilative reactions. For example, it is known that vasoconstriction can be induced by mechanical loads such as vascular stretch and increased vascular inner pressure, by such agents as thrombin and by hypoxemia, and further that noradrenaline-induced vasoconstriction can be enhanced by use of neuropeptide Y [*Proc. Natl. Acad. Sci. U.S.A.* 79, 5485 (1982); ibid. 81, 4577 (1984)].

Endothelial cell-derived coronary vascular constrictor factors (each having molecular weights of 8,500 and 3,000) are described in *Amer. J. Physiol.* 248, c550 (1985) and *J. Cell Physiol.* 132, 263 (1987). However, their sequences are unknown. An endothelial cell-derived peptide-like substance is also described in *J. Pharmacl. Exp. Ther.* 236, 339 (1985). However, the sequence of that substance is also unknown.

On the other hand, vasopressin is known as a peptide having a vasoconstrictor activity. The amino acid sequence of vasopression has been determined. There have been no reports, however, that vasopressin was obtained from mammalian or bird vascular endothelial cells. Although there is a report that an angiotensin having a vasoconstrictor activity was obtained from the endothelial cells of bovine aortas [*Circulation Research* 60, 422 (1987)], the angiotensin is a peptide having a molecular weight of only about 1,000.

Some of the present inventors have previously succeeded in isolating porcine endothelin as a peptide having a similar vasoconstrictor activity from the endothelial cells of porcine aortas (Japanese Patent Application No. 255381/1987). Some of the present inventors have also succeeded in isolating human endothelin and cloning porcine endothelin cDNA and human endothelin cDNA (Japanese Patent Application Nos. 275613/1987, 313155/1987 and 148158/1988). The mature polypeptides of the porcine endothelin and the human endothelin have the same amino acid sequence, and are referred to as endothelin-1.

Further, the present inventors have filed patent applications with respect to the isolation of rat endothelin and the cloning of its cDNA (Japanese Patent Application Nos. 174935/1988 and 188083/1988), and this is referred to as endothelin-3.

Furthermore, the present inventors have also filed a patent application with respect to the cloning of human endothelin-3 (Japanese Patent Application No. 278497/1989).

Moreover, the present inventors have also filed a patent application with respect to the isolation of mouse endothelin and the cloning of its cDNA (Japanese Patent Application No. 223389/1988), and this is referred to as endothelin B.

In addition, the present inventors have cloned, from a genomic human library, a DNA coding for endothelin having an amino acid sequence different from that of endothelin-1 which has been named endothelin-2, and have filed a patent application with respect to a protein of endothelin-2 and its DNA (Japanese Patent Application No. 274990/1989).

The amino acid sequences of these endothelin-1 (SEQ ID NO:3), endothelin B (SEQ ID NO:4), endothelin-3 (SEQ ID NO:5) and endothelin-2 (SEQ ID NO:6) are shown in FIG. 1 in comparison to one another.

Endothelin is a general term for peptides having a molecular weight of 2500±300 and having 21 amino acid residues, including four cysteine groups located at the 1st, 3rd, 11th and 15th residues from the N-terminus of the amino acid sequence, which form two sets of disulfide bonds. One of the combinations of the disulfide bonds may be 1–15 and 3–11 cysteine groups, and the other may be 1–11 and 3–15. The former combination is higher in ratio of formation and in activity than the latter combination.

As described above, homologous endothelin peptides have been discovered from various animals. However, no novel homologous genes have been discovered from the same animal species. It is therefore a current subject that novel homologous endothelin is further screened, and the structure and activity of the endothelin are studied, thereby examining its usefulness, and that the novel peptide is cloned by recombinant DNA technology to allow mass production thereof.

SUMMARY OF THE INVENTION

The present inventors have variously studied, considering that important contributions will be made to future studies and medical treatments, if a novel homologous gene having the vasoconstrictor activity described above can be isolated and further prepared by recombinant DNA technology. As a result, the following information has been obtained, thus arriving at the present invention.

Namely, the present inventors have succeeded in cloning cDNA (complementary DNA) coding for endothelin having an amino acid sequence different from those of the above endothelin-1 and endothelin-3 [human endothelin (endothelin A) and endothelin-3] from a human cDNA library by using as a probe the synthesized DNA segment coding for a portion of genomic DNA of the human endothelin described in the patent applications previously filed and a DNA comprising an about 99-bp genomic DNA segment of endothelin-2, and consequently in pioneering its mass production by recombinant technology. The present inventors further provide a precursor of human endothelin-2 having a novel amino acid sequence.

In accordance with the present invention, there are provided (1) a DNA containing a cDNA segment coding for human endothelin-2, (2) a precursor of human endothelin-2, (3) a transformant carrying a DNA containing a cDNA segment coding for human endothelin-2, and (4) a method for preparing mature human endothelin-2 which comprises culturing the transformant described in (3), accumulating a protein in a culture medium, and collecting the same.

BRIEF DESCRIPTION OF THE DRAWINGS

FIG. 1 shows amino acid sequences of various endothelin peptides in comparison to one another;

FIGS. 3-1 through 3-3 shows a nucleotide sequence (SEQ ID NO:1) of the cDNA segment coding for human endothelin-2 obtained in the present invention and an amino acid sequence (SEQ ID NO:2) ascertained from that nucleotide sequence;

FIG. 4 shows an amino acid sequence of a precursor of human endothelin-2 (SEQ ID NO:2);

DESCRIPTION OF THE PREFERRED EMBODIMENTS

Figure 2:
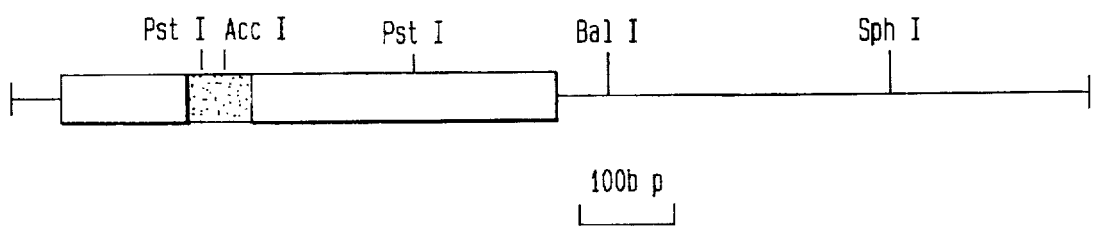
FIG. 2 shows a restriction enzyme fragment map of a cDNA segment coding for human endothelin-2 obtained in the present invention.

The cDNA segment contained in the DNA of the present invention which codes for human endothelin-2 contains a nucleotide sequence (SEQ ID NO: 1) represented by the following formula [1] or is a portion thereof. This CDNA segment is different from the known ones and novel.

Formula [1]

| | | | | | | | | | | |
|---|---|---|---|---|---|---|---|---|---|---|
| 1 | A | GGA | CGC | TGG | CAA | CAG | GCA | CTC | CCT | GCT | 28 |
| 29 | CCA | GTC | CAG | CCT | GCC | CGC | TCC | ACC | GCC | GCT | 58 |
| 59 | ATG | GTC | TCC | GTG | CCT | ACC | ACC | TGG | TGC | TCC | 88 |
| 1 | M | V | S | V | P | T | T | W | C | S | 10 |
| 89 | GTT | GCG | CTA | GCC | CTG | CTC | GTG | GCC | CTG | CAT | 118 |
| 11 | V | A | L | A | L | L | V | A | L | H | 20 |
| 119 | GAA | GGG | AAG | GGC | CAG | GCT | GCT | GCC | ACC | CTG | 148 |
| 21 | E | G | K | G | Q | A | A | A | T | L | 30 |
| 149 | GAG | CAG | CCA | GCG | TCC | TCA | TCT | CAT | GCC | CAA | 178 |
| 31 | E | Q | P | A | S | S | S | H | A | Q | 40 |
| 179 | GGC | ACC | CAC | CTT | CGG | CTT | CGC | CGT | TGC | TCC | 208 |
| 41 | G | T | H | L | R | L | R | R | C | S | 50 |
| 209 | TGC | AGC | TCC | TGG | CTC | GAC | AAG | GAG | TGC | GTC | 238 |
| 51 | C | S | S | W | L | D | K | E | C | V | 60 |
| 239 | TAC | TTC | TGC | CAC | TTG | GAC | ATC | ATC | TGG | GTG | 268 |
| 61 | Y | F | C | H | L | D | I | I | W | V | 70 |
| 269 | AAC | ACT | CCT | GAA | CAG | ACA | GCT | CCT | TAC | GGG | 298 |
| 71 | N | T | P | E | Q | T | A | P | Y | G | 80 |
| 299 | CTG | GGA | AAC | CCG | CCA | AGA | CGC | CGG | CGC | CGC | 328 |
| 81 | L | G | N | P | P | R | R | R | R | R | 90 |
| 329 | TCC | CTG | CCA | AGG | CGC | TGT | CAG | TGC | TCC | AGT | 358 |
| 91 | S | L | P | R | R | C | Q | C | S | S | 100 |
| 359 | GCC | AGG | GAC | CCC | GCC | TGT | GCC | ACC | TTC | TGC | 388 |
| 101 | A | R | D | P | A | C | A | T | F | C | 110 |
| 389 | CTT | CGA | AGG | CCC | TGG | ACT | GAA | GCC | GGG | GCA | 418 |
| 111 | L | R | R | P | W | T | E | A | G | A | 120 |
| 419 | GTC | CCA | AGC | CGG | AAG | TCC | CCT | GCA | GAC | GTG | 448 |
| 121 | V | P | S | R | K | S | P | A | D | V | 130 |
| 449 | TTC | CAG | ACT | GGC | AAG | ACA | GGG | GCC | ACT | ACA | 478 |

-continued
Formula [1]

| 131 | F | Q | T | G | K | T | G | A | T | T | 140 |
| --- | --- | --- | --- | --- | --- | --- | --- | --- | --- | --- | --- |
| 479 | GGA | GAG | CTT | CTC | CAA | AGG | CTG | AGG | GAC | ATT | 508 |
| 141 | G | E | L | L | Q | R | L | R | D | I | 150 |
| 509 | TCC | ACA | GTC | AAG | AGC | CTC | TTT | GCC | AAG | CGA | 538 |
| 151 | S | T | V | K | S | L | F | A | K | R | 160 |
| 539 | CAA | CAG | GAG | GCC | ATG | CGG | GAG | CCT | CGG | TCC | 568 |
| 161 | Q | Q | E | A | M | R | E | P | R | S | 170 |
| 569 | ACA | CAT | TCC | AGG | TGG | AGG | AAG | AGA | TAG | TGT | 598 |
| 171 | T | H | S | R | W | R | K | R | * | | 179 |
| 599 | CGT | GAG | CTG | GAG | GAA | CAT | TGG | GAA | GGA | AGC | 628 |
| 629 | CCG | CGG | GGA | GAG | AGG | AGG | AGA | GAA | GTG | GCC | 658 |
| 659 | AGG | GCT | TGT | GGA | CTC | TCT | GCC | TGC | TTC | CTG | 688 |
| 689 | GAC | CGG | GGC | CTT | GGT | CCC | AGA | CAG | CTG | GAC | 718 |
| 719 | CCA | TTT | GCC | AGG | ATT | GGC | ACA | AGC | TCC | CTG | 748 |
| 749 | GTG | AGG | GAG | CCT | CGT | CCA | AGG | CAG | TTC | TGT | 778 |
| 779 | GTC | CTC | GCA | CTG | CCC | AGG | GAA | GCC | CTC | GGC | 808 |
| 809 | CTC | CAG | ACT | GCG | GAG | CAG | CCT | CCA | GTG | CTG | 838 |
| 839 | GCT | GCT | GGC | CCA | CAG | CTC | TGC | TGG | AAG | AAC | 868 |
| 869 | TGC | ATG | GGG | AGT | ACA | TTC | ATC | TGG | AGG | CTG | 898 |
| 899 | CGT | CCT | GAG | GAG | TGT | CCT | GTC | TGC | TGG | GCT | 928 |
| 929 | ACA | AAC | CAG | GAG | CAA | CCG | TGC | AGC | CAC | GAA | 958 |
| 959 | CAC | GCA | TGC | CTC | AGC | CAG | CCC | TGG | AGA | CTG | 988 |
| 989 | GAT | GGC | TCC | CCT | GAG | GCT | GGC | ATC | CTG | GCT | 1018 |
| 1019 | GGC | TGT | GTC | CTC | TCC | AGC | TTT | CCC | TCC | CCA | 1048 |
| 1049 | GAG | TTG | TTG | CAC | CCT | CAT | TCC | CTC | GGG | ACC | 1078 |
| 1079 | CTC | CCA | GTG | AGA | AGG | GCC | TGC | TCT | GCT | TTT | 1108 |
| 1109 | CCT | GTC | TGT | ATA | TAA | CTT | ATT | TGC | CCT | AAG | 1138 |
| 1139 | AAC | TTT | GAG | AAT | CCC | AAT | TAT | TTA | TTT | TAA | 1168 |
| 1169 | TGT | ATT | TTT | TAG | ACC | CTC | TAT | TTA | CCT | GCG | 1198 |
| 1199 | AAC | TTG | TGT | TTA | TAA | AT | | | | | 1218 |

The precursor of human endothelin-2 of the present invention contains an amino acid sequence (SEQ ID NO:2) represented by the following formula [2]:

Formula [2]

```
         10           20           30           40           50           60
N-MVSVPTTWCSVALALLVALHEGKGQAAATLEQPASSSHAQGTHLRLRRCSCSSWLDKECV 70           80           90          100          110          120
YFCHLDIIWVNTPEQTAPYGLGNPPRRRRRSLPRRCQCSSARDPACATFCLRRPWTEAGA 130          140          150          160          170
VPSRKSPADVFQTGKTGATTGELLQRLRDISTVKSLFAKRQQEAMREPRSTHSRWRKR*-C
```

A protein having a sequence corresponding to the sequence of the 49th to the 85th amino acids in formula 2, a sequence represented by the following formula, is also a kind of precursor of human endothelin-2, and called big endothelin-2(1–37).

C S C S S W L D K E C V Y F C H L D I I W V N T P E Q T
A P Y G L G N P P (SEQ ID NO:7)

A protein having a sequence corresponding to the sequence of the 49th to the 86th amino acids in formula 2, a sequence represented by the following formula, is also a kind of precursor of human endothelin-2, and called big endothelin-2(1–38).

C S C S S W L D K E C V Y F C H L D I I W V N T P E Q T
A P Y G L G N P P R (SEQ ID NO:8)

The nucleotide sequence represented by formula [1] (SEQ ID NO:1) is the sequence of the human endothelin-2 cDNA obtained in the present invention. Examples of the nucleotide sequences coding for the mature human endothelin-2 amino acids represented by formula [2] (SEQ ID NO:2) (the above underlined sequence of C S C S S W L D K E C V Y F C H L D I I W) include the sequence represented by Nos. 203 to 265 in formula [1] (SEQ ID NO:1).

In the present invention, for example, an expression vector having the DNA sequence containing the nucleotide sequence coding for mature human endothelin-2 can be prepared by the following process:

(a) Messenger RNA (mRNA) is isolated from human endothelin-2-producing cells.

(b) Single stranded complementary DNA (cDNA) is synthesized from the mRNA, followed by synthesis of double stranded DNA.

(c) The complementary DNA is introduced in a cloning vector such as a phage or a plasmid.

(d) Host cells are transformed with the recombinant phage or plasmid thus obtained.

(e) After cultivation of the transformants thus obtained, the plasmids or the phages containing the desired DNA is isolated from the transformant by an appropriate method such as hybridization with a DNA probe coding for a portion of human endothelin-2 or immunoassay using an anti-human endothelin-2 antibody.

(f) The desired cloned DNA sequence is cleaved from the recombinant DNA.

(g) The cloned DNA sequence or a portion thereof is ligated downstream from a promoter in the expression vector.

The MRNA coding for human endothelin-2 can be obtained from various endothelin-producing cells such as ACHN cells of human renal cancer cells.

Methods for preparing the mRNA from the human endothelin-2-producing cells include the guanidine thiocyanate method [J. M. Chirgwin et al., Biochemistry 18, 5294 (1979)] and the like.

Using the MRNA thus obtained as a template, cDNA is synthesized by use of reverse transcriptase, for example, in accordance with the method of H. Okayama et al. [Molecular and Cellular Biology 2, 161 (1979); and ibid. 3, 280 (1983)]. The cDNA thus obtained is introduced into the plasmid.

The plasmids into which the cDNA may be introduced include, for example, pBR322 [Gene 2, 95 (1977)], pBR325 [Gene 4, 121 (1978)], pUC12 [Gene 19, 259 (1982)], pUC13 [Gene 19, 259 (1982)], pUC118 and pUC119, each derived from Escherichia coli, and pUB110 derived from Bacillus subtilis [Biochemical and Biophysical Research Communication 112, 678 (1983)]. However, any other plasmid can be used as long as it is replicable and growable in the host cell. Examples of the phage vectors into which the cDNA may be introduced include gtll [R. Young and R. Davis, Proc. Natl. Acad. Sci. U.S.A. 80, 1194 (1983)]. However, any other phage vector can be used as long as it is growable in the host cell.

Methods for introducing the cDNA into the plasmid include, for example, the method described in T. Maniatis et al., Molecular Cloning, Cold Spring Harbor Laboratory, p.239 (1982). Methods for introducing the cDNA into the phage vector include, for example, the method of T. V. Hyunh et al. [DNA Cloning, A Practical Approach 1, 49 (1985)].

The plasmid thus obtained is introduced into an appropriate host cell such as Escherichia and Bacillus.

Examples of Escherichia described above include Escherichia coli K12DH1 [Proc. Natl. Acad. Sci. U.S.A. 60, 160 (1968)], M103 [Nucleic Acids Research 9, 309 (1981)), JA221 [Journal of Molecular Biology 120, 517 (1978)], HB101 [Journal of Molecular Biology 41, 459 (1969)] and C600 [Genetics 39, 440 (1954)].

Examples of Bacillus described above include Bacillus subtilis MI114 [Gene 24, 255 (1983)] and 207–21 [Journal of Biochemistry 95, 87 (1984)].

Methods for transforming the host cell with the plasmid include, for example, the calcium chloride method or the calcium chloride/rubidium chloride method described in T. Maniatis et al., Molecular Cloning, Cold Spring harbor Laboratory, p.249 (1982).

When the phage vector is used, for example, it can be transduced into proliferated E. coli, using the in vitro packaging method [T. Maniatis et al., Molecular Cloning, A Laboratory Manual, Coldspringharbor, 1982, pp.262–268].

Human cDNA libraries containing human endothelin-2 cDNA can be obtained by the above-mentioned methods and the like.

Methods for cloning human endothelin-2 cDNA from the human DNA library include, for example, the plaque hybridization method using phage vector λcharon 4A and an oligonucleotide chemically synthesized on the basis of the amino acid sequence of human endothelin-2 as a probe [T. Maniatis et al., *Molecular Cloning*, Cold Spring Harbor Laboratory, (1982)]. The human endothelin-2 cDNA thus cloned may be subcloned, for example, in pBR322, pUC12, pUC13, pUC18, pUC19, pUC118 and pUC119 to obtain the human endothelin-2 cDNA, if necessary.

The nucleotide sequence of the DNA sequence thus obtained is determined, for example, by the Maxam-Gilbert method [A. M. Maxam and W. Gilbert, *Proc. Natl. Acad. Sci. U.S.A.* 74, 560 (1977)] or the dideoxy method [J. Messing et al., *Nucleic Acids Research* 9, 309 (1981)], and the existence of the human endothelin-2 DNA is confirmed in comparison with the known amino acid sequence.

As described above, the cDNA (human endothelin-2 cDNA) represented by formula [1] (SEQ ID NO:1) coding for human endothelin-2 is obtained.

FIG. 2 shows the restriction enzyme fragment map of the cDNA coding for human endothelin-2 obtained in Example 2 described below. FIG. 3 shows the nucleotide sequence of the cDNA as determined by the dideoxy method (SEQ ID NO:1), and the amino acid sequence deduced from that nucleotide sequence. FIG. 4 shows the amino acid sequence of a precursor of human endothelin-2 (SEQ ID NO:2).

The cDNA coding for human endothelin-2 cloned as described above can be used as it is, or after digestion with a restriction enzyme if desired, depending on the intended use.

A region intended to be expressed is cleaved from the cloned cDNA and ligated downstream from the promoter in a vehicle (vector) suitable for expression, whereby the expression vector can be obtained.

The cDNA has ATG as a translation initiating codon at the 5'-terminus thereof and may have TAA, TGA or TAG as a translation terminating codon at the 3'-terminus. The translation initiating codon and translation terminating codon may be added by use of an appropriate synthetic cDNA adaptor. The promoter is further ligated upstream therefrom for the purpose of expressing the cDNA.

Examples of the vectors include the above plasmids derived from *E. coli* such as pBR322, pBR325, pUC12 and pUC13, the plasmids derived from *Bacillus subtilis* such as pUB110, pTP5 and pC194, plasmids derived from yeast such as pSH19 and pSH15, bacteriophages such as λphage, and animal viruses such as retroviruses and vaccinia viruses.

As the promoter used in the present invention, any promoter is available as long as it is suitable for expression in the host cell selected for the gene expression.

When the host cell used for transformation is Escherichia, it is preferable that a trp promoter, a lac promoter, a recA promoter, a λPL promoter, a lpp promoter, etc. are used. When the host cell is Bacillus, it is preferable that a PHO5 promoter, a PGK promoter, a GAP promoter, an ADH promoter, etc. are used. In particular, it is preferable that the host cell is Escherichia and the promoter is the trp promoter or the λPL promoter.

When the host cell is an animal cell, a SV-40 derived promoter, a retrovirus promoter, a metallothionein promoter, a heat shock promoter, etc. are each usable.

An enhancer is also effectively used for expression.

Using a vector containing the cDNA coding for the human endothelin-2 mature peptide thus constructed, transformants are prepared.

The host cells include, for example, Escherichia, Bacillus, yeast and animal cells.

As specific examples of the above Escherichia and Bacillus, strains similar to those described above can be mentioned.

Examples of the above yeast include *Saccharomyces cetevisiae* AH22, AH22R⁻, NA87-11A and DKD-5D.

Examples of the animal cells include monkey cell COS-7, Vero, Chinese hamster cell (CHO), mouse L cell and human FL cell.

The transformation of the above Escherichia is carried out according to, for example, the method described in *Proc. Natl. Acad. Sci. U.S.A.* 69, 2110 (1972).

The transformation of the above Bacillus is conducted according to, for example, the method described in *Molecular & General Genetics* 168, 111 (1979).

The transformation of the yeast is carried out according to, for example, the method described in *Proc. Natl. Acad. Sci. U.S.A.* 75, 1929 (1978).

The transformation of the animal cells is carried out according to, for example, the method described in *Virology* 52, 456 (1973).

Thus, transformants are obtained which are transformed with an expression vector containing the cDNA coding for the human endothelin-2 mature peptide.

When bacterial transformants are cultured, a liquid medium is particularly suitable as a medium used for culture. Carbon sources, nitrogen sources, inorganic compounds and others necessary for growth of the transformants are contained therein. Examples of the carbon sources include glucose, dextrin, soluble starch and sucrose. Examples of the nitrogen sources include inorganic or organic materials such as ammonium salts, nitrates, corn steep liquor, peptone, casein, meat extracts, soybean meal and potato extract solution. The inorganic compounds include, for example, calcium chloride, sodium dihydrogenphosphate and magnesium chloride. Yeast, vitamins, growth promoting factors and so on may be further added thereto.

The pH of the medium is preferably about 5 to 8.

As the medium used for cultivation of Escherichia, for example, M9 medium containing glucose and Casamino Acids (Miller, *Journal of Experiments in Molecular Genetics* 431–433, Cold Spring Harbor Laboratory, New York, 1972) is preferably used. In order to make the promoter act efficiently, a compound such as 3-indolylacrylic acid may be added thereto if necessary.

When the host cell is Escherichia, the cultivation is usually carried out at about 15° to 43° C. for about 3 to 24 hours, with aeration or agitation if necessary.

When the host cell is Bacillus, the cultivation is usually carried out at about 30° to 40° C. for about 6 to 24 hours, with aeration or agitation if necessary.

When yeast transformants are cultured, for example, Burkholder minimum medium [K. L. Bostian et al., *Proc. Natl. Acad. Sci. U.S.A.* 77, 4505 (1980)] is used as the medium. The pH of the medium is preferably adjusted to about 5 to 8. The cultivation is usually carried out at about 20° to 35° C. for about 24 to 72 hours, with aeration or agitation if necessary.

When animal cell transformants are cultured, examples of the media include MEM medium containing about 5 to 20% fetal calf serum [*Science* 122, 501 (1952)], DMEM medium [*Virology* 8, 396 (1959)], RPMI1640 medium (*The Journal of the American Medical Association* 199, 519 (1967)] and 199 medium [*Proceeding of the Society for the Biological Medicine* 73, 1 (1950). The pH is preferably about 6 to 8. The cultivation is usually carried out at about 30° to 40° C. for about 15 to 60 hours, with aeration or agitation if necessary.

The human endothelin-2 mature peptide (endothelin-2) can be isolated and purified from the culture described above, for example, by the following method.

When the human endothelin-2 mature peptide is extracted from the cultured cells, the cells are collected by methods known in the art after cultivation. Then, the collected cells are suspended in an appropriate buffer solution and disrupted by ultrasonic treatment, lysozyme and/or freeze-thawing. Thereafter, a crude extracted solution of the human endothelin-2 mature peptide is obtained by centrifugation or filtration. The buffer solution may contain a protein denaturant such as urea or guanidine hydrochloride, or a surface-active agent such as Triton X-100.

When the human endothelin-2 precursor protein or mature peptide is secreted in the culture solution, a supernatant is separated from the cells by methods known in the art after the conclusion of cultivation, and then collected.

The separation and purification of the human endothelin-2 precursor protein or mature peptide contained in the culture supernatant or the extracted solution thus obtained can be performed by an appropriate combination of separating and purifying methods known in the art. The known separating and purifying methods include methods utilizing solubility such as salt precipitation and solvent precipitation, methods mainly utilizing a difference in molecular weight such as dialysis, ultrafiltration, gel filtration and SDS-polyacrylamide gel electrophoresis, methods utilizing a difference in electric charge such as ion-exchange column chromatography, methods utilizing specific affinity such as affinity chromatography, methods utilizing a difference in hydrophobicity such as reverse phase high performance liquid chromatography and methods utilizing a difference in isoelectric point such as isoelectro-focussing electrophoresis.

The activity of the human endothelin-2 precursor protein or mature peptide thus formed can be measured by an enzyme immunoassay using a specific antibody. If the products have vasoconstrictive activity, the human endothelin-2 precursor protein or mature peptide may also be measured based thereupon.

The cells transfected or transformed with the DNA of the present invention allow large amounts of the human endothelin-2 mature peptide to be produced. Hence, the production of these peptides can be advantageously achieved.

Like the other endothelin peptides, endothelin-2 and the precursor thereof prepared here not only can be utilized as a hypotonia therapeutic agent or a topical vasoconstrictor, but can also be utilized to analyze the mechanism of the vasoconstrictor reactions in vivo and to elucidate the antagonists to the vasoconstrictor factors. Similarly, the peptides have such effects as preventing various kinds of hemorrhage, for example, gastric or esophageal hemorrhage as a vasoconstrictor, and may also be useful in curing various shock symptoms. These peptides can be administered orally, locally, intravenously or parenterally, preferably topically or intravenously. The dose is 0.001 µg to 100 µg/kg, and preferably 0.01 µg to 10 µg/kg. The peptides are used in dose dependent on weight and in the form of a solution in 1 to 10 ml of physiological saline.

The peptides of the present invention can be formed into various preparations together with additional components, such as emulsions, hydrated mixtures, tablets, solutions, powders, granules, capsules and pills. Examples of the additional components include pharmaceutically acceptable excipients, disintegrators, lubricants, binders, dispersants, plasticizers, fillers and carriers. As to the additional components, examples of the excipients include lactose, glucose and white sugar; those of the disintegrators include starch, sodium alginate, agar powder and carboxymethyl cellulose calcium; those of the lubricants include magnesium stearate, talc and liquid paraffin; those of the binders include syrup, gelatin solution, ethanol and polyvinyl alcohol; those of the dispersants include methyl cellulose, ethyl cellulose and shellac; and those of the plasticizers include glycerin and starch.

When nucleotides, amino acids and so on are indicated by abbreviations in this specification and drawings, the abbreviations adopted by the IUPAC-IUB Commission on Biochemical Nomenclature or commonly used in the art are employed. For example, the following abbreviations are used. When the amino acids are capable of existing as optical isomers, it is understood that the L-forms are represented unless otherwise specified.

| DNA: | Deoxyribonucleic acid |
|---|---|
| cDNA: | Complementary deoxyribonucleic acid |
| A: | Adenine |
| T: | Thymine |
| G: | Guanine |
| C: | Cytosine |
| RNA: | Ribonucleic acid |
| mRNA: | Messenger ribonucleic acid |
| dATP: | Deoxyadenosine triphosphate |
| dTTP: | Deoxythymidine triphosphate |
| dGTP: | Deoxyguanosine triphosphate |
| dCTP: | Deoxycytidine triphosphate |
| ATP: | Adenosine triphosphate |
| EDTA: | Ethylenediaminetetraacetic acid |
| SDS: | Sodium dodecyl sulfate |
| Gly or G: | Glycine |
| Ala or A: | Alanine |
| Val or V: | Valine |
| Leu or L: | Leucine |
| Ile or I: | Isoleucine |
| Ser or S: | Serine |
| Thr or T: | Threonine |
| Cys or C: | Cysteine |
| Met or M: | Methionine |
| Glu or E: | Glutamic acid |
| Asp or D: | Aspartic acid |
| Lys or K: | Lysine |
| Arg or R: | Arginine |
| His or H: | Histidine |
| Phe or F: | Phenylalanine |
| Tyr or Y: | Tyrosine |
| Trp or W: | Tryptophan |
| Pro or P: | Proline |
| Asn or N: | Asparagine |
| Gln or Q: | Glutamine |

With respect to human endothelin-2 of the present invention, a portion of the amino acid sequence may be modified, namely there may be addition, elimination or substitution with other amino acids as long as the vasoconstrictor property is not lost.

The present invention will hereinafter be described in more detail with the following Reference Example and Examples. It is understood of course that these Reference Example and Examples are not intended to limit the scope of the invention.

Transformant *E. coli* MV1184/pHET-2(K) obtained in Example 3 was deposited with the Institute for Fermentation, Osaka, Japan (IFO) under the accession number IFO 15064 on Jul. 10, 1990, and also deposited with the Fermentation Research Institute, the Agency of Industrial Science and Technology, the Ministry of International Trade and Industry, Japan (FRI) under the accession number FERM BP-3008 on Jul. 12, 1990.

Transformant E. coli MC1061/P3/pTS612 obtained in Example 5 was deposited with the Institute for Fermentation, Osaka, Japan (IFO) under the accession number IFO 15122 on Dec. 24, 1990, and also deposited with the Fermentation Research Institute, the Agency of Industrial Science and Technology, the Ministry of International Trade and Industry, Japan (FRI) under the accession number FERM BP-3211 on Dec. 20, 1990.

Reference Example (1) Assay of Vascular Smooth Muscle Constrictor Activity

Porcine right coronary artery spiral specimens (0.5×20 mm) with the intima denuded by rubbing with a small swab are suspended in 3 ml of Krebs-Ringer solution maintained at 37° C. and saturated with a mixed gas containing 5% carbon dioxide and 95% oxygen by volume. After setting the basal tension to 2 g, the isometric tension is measured with a tension transducer.

(2) Assay of Cardiotonic Action

Instead of the porcine right coronary artery spiral specimens used in the assay described in the above item (1), suspended guinea pig right atrium specimens are used, and the tension and the heart rate per minute are measured according to the same procedure as described in (1).

EXAMPLE 1

Preparation of DNA Probe Coding for a Portion of DNA of Genomic Human Endothelin-2

A DNA probe coding for a portion of the DNA sequence of genomic human endothelin-2, which had the following sequence, was chemically synthesized, and used for hybridization with an ACHN cell-derived cDNA library.

5' CATGCCCAAGGCACCCACCTTCGGCT-
TCGCCGTTGCTCCTGCAGCTCCTG GCTCGA-
CAAGGAGTGCGTCTACTTCTGCCACTTG-
GACATCATCTGGGTG 3'(SEQ ID NO:9)

EXAMPLE 2

Extraction of MRNA and Preparation of cDNA Library (1) Extraction of Total RNA from ACHN Cells Human renal cancer cells, ACHN (ATCC, CRL 1611), were cultured in Dulbecco's minimum essential medium (D-MEM) containing 10% fetal calf serum in an atmosphere of 5% $CO_2$ and 95% air at 37° C. [for ten 150-$cm^2$ flasks (Falcon)]. After 3 to 4 days, the culture solution was removed, followed by washing with phosphate buffered saline (PBS). Then, 100 ml per flask of a guanidine-isothiocyanate solution (5M guanidine-isothiocyanate, 50 mM Tris-HCl, 10 mM EDTA and 5% mercaptoethanol) was added thereto to solve the cells, followed by collection in a 150-ml glass homogenizer and sufficient trituration.

A 20% sodium sarcosinate solution (20% sodium N-lauroylsarcosinate, 50 mM Tris-HCl (pH 7.6), 10 mM EDTA and 5% mercaptoethanol) was added to a final concentration of 5%, followed by further sufficient trituration. Solid cesium chloride was added thereto to a concentration of 0.2 g/ml, followed by further sufficient trituration while dissolving it. Then, 5 ml of a 5.2M solution of cesium chloride in 0.5M ethylenediaminetetraacetic acid (EDTA) was placed in a tube for an SW28 rotor (Beckmann), and 30 ml of the above-mentioned cell solution was layered thereon, followed by centrifugation with the SW28 rotor at 28,000 rpm at 22° C. for 48 hours.

RNA was collected on pellets in the tube, and an upper layer solution was removed by absorption according to the method of Kaplain [Biochem. J. 183, 181–184 (1979)]. Then, after the RNA was dissolved in a 0.4% sarcosine solution, NaCl was added thereto to a final concentration of 0.25M. Cold ethanol was added thereto in an amount of 2.5 volumes, and the resulting solution was stored at –20°.

(2) Separation of $PolyA^+$ RNA

Total RNAs were collected by centrifugation (at 25,000 rpm for 20 minutes), and $polyA^+$ RNA was partially purified by oligo(dt) column chromatography according to the manual of the method for purifying polyA RNA (Pharmacia). About 5% of the total RNAs was recovered as the $polyA^+$ RNA.

(3) Synthesis of cDNA and Preparation of cDNA Library by Using Phage λgtll cDNA was synthesized from 5 µg of the $polyA^+$ RNA obtained in (2) described above, using a cDNA synthesizing kit (Amersham) according to the manual, and using $^{32}P$-dCTP as a marker for cDNA synthesis. About 10% of 5 µg of the $polyA^+$ RNA used was obtained as double-stranded DNA (ds DNA).

Similarly using a CDNA cloning kit (Amersham), adapters for restriction enzyme EcoRI were ligated to this ds DNA by the ligation reaction, and treated with EcoRI to obtain ds DNA to the 5'- and 3'-termini of which EcoRI adapters were ligated.

The cDNA to which the EcoRI adapters were ligated was introduced into the EcoRI site of phage λgtll DNA, and reconstructed to phage particles, thereby obtaining a cDNA library of phage λgtll. The resulting cDNA library of phage λgtll exhibited an infection value of about $2×10^6$ plaque forming units/ml.

EXAMPLE 3

Cloning of Human Endothelin-2 CDNA and Isolation of Phage Clones Having Human Endothelin-2 cDNA The recombinant phage (λgtll) obtained in (3) of Example 2 was transfected in E. coli Y1090 under a condition of 1,500 plaques/Schale by the method of Pentone and Davis (Science 196, 180–182 (1977)], and then the phage was transferred to a nitrocellulose filter. The filter was treated according to the method of Benton and Davis [W. D. Benton and R. W. Davis, Science, 196, p.180 (1977)]. A partial DNA fragment having a nucleic acid sequence [Inoue et al., Proc. Natl. Acad. Sci. U.S.A. 86, 2863–2867 (1989)] coding for endothelin-2 of genomic human DNA, which had the following sequence (SEQ ID NO:9), was synthesized with a DNA synthesizer (Model AB1), and a $^{32}P$-labeled probe was prepared by the random priming method using α-$^{32}P$.dCTP.

5' CATGCCCAAGGCACCCACCTTCGGCT-
TCGCCGTTGCTCCTGCAGCTCCTG GCTCGA-
CAAGGAGTGCGTCTACTTCTGCCACTTG-
GACATCATCTGGGTG 3'

The recombinant phage DNA transferred to the nitrocellulose filter was hybridized with the $^{32}P$-labeled endothelin-2 probe by the method of Pentone and Davis [Science 196, 180–182 (1977)]. Phage clones which formed hybrids were screened to obtain several positive plaques. The cloned phage was transfected in E. coli Y1090 in LB broth at 37° C. for 5 to 6 hours. After removal of E. coli by centrifugation. 200 µl of a 20% polyethylene glycol 0.15M NaCl solution was added to 1 ml of the culture solution, followed by standing at 4° C. for 2 to 3 hours. Then, phage particles were precipitated by centrifugation at 15,000 rpm for 20 minutes. The phage particles were suspended by addition of 100 µl of distilled water, and the resulting suspension was heated at 95° C. for 10 minutes. This recombinant phage DNA was λgtll. Hence, using the DNA fragments of 5' GGTGGCGACGACTCCTGGAGCCCG (SEQ ID NO:10) and 5' TTGACACCAGACCAACTGG-TAATG (SEQ ID NO:11) close to the EcoRI site, a recombinant site of cDNA, as primers for λgtll, this cDNA portion was obtained by amplification according to the polymer chain reaction (PCR) method [I. A. Michael and Iunis, *PCR Protocols*, Academic Press (1990)].

The DNA obtained by amplification synthesis according to the PCR method was treated with EcoRI, followed by ligation to the EcoRI site of plasmid pUC118 by the ligation reaction. Then, *E. coli* DH5α was transformed into 5 clones shown below:

pHET-2(52)/*E. coli* MV1184
pHET-2(31)/*E. coli* MV1184
pHET-2(27)/*E. coli* MV1184
pHET-2(26)/*E. coli* MV1184
pHET-2(35)/*E. coli* MV1184

Of these clones, pHET-2(52)/*E. coli* MV1184 is referred to as pHET/2(K)/*E. coli* MV1184.

EXAMPLE 4

Determination of Nucleotide Sequence of Cloned DNA

The plasmid DNA obtained in Example 3 described above was purified, and the nucleotide sequence of the DNA was determined by the dideoxy-chain termination method [*Proc. Natl. Acad. Sci. U.S.A.* 74, 5463–5467 (1977)]. The determination direction and the whole nucleotide sequence (SEQ ID NO:1) thereof are shown in FIG. 3.

The cDNA coding for the precursor of human endothelin-2 is pHET-2(52) and consists of 1218 nucleotides. An open frame of 534 nucleotides is removed therefrom to code for 178 amino acid residues. The portion being boxed is the portion of human endothelin-2, and identical with the sequence previously shown from the sequence of the genomic DNA.

EXAMPLE 5

Expression of Human Endothelin-2

Figure 5:
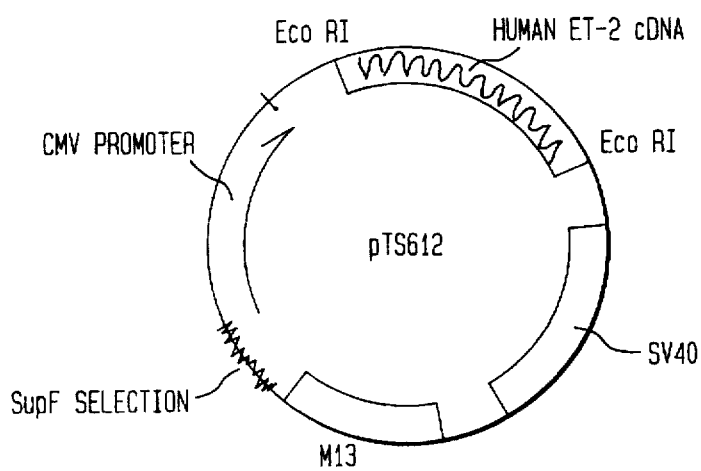
FIG. 5 is a schematic representation showing the construction of a plasmid for expression of human endothelin in Example 5.

Plasmid pHET-2(K) having cDNA coding for the precursor of human endothelin-2 was cleaved with the restriction enzyme EcoRI and introduced into the EcoRI site of expression vector pcDNA. Then, *E. coli* MC1061/P3 was transformed to obtain *E. coli* MC1061/P3/pTS612 (FIG. 5). This plasmid was purified and allowed to be entrapped in CHO-K1 cells together with plasmid pSV2neo according to the method of McCutchan and Pagano [J. H. McCutchan and J. S. Pagano, J. of the National Cancer Institute, 41(2), pp. 351–357 (1968)]. Then, drug G418-resistant cells were selected. The cells were cloned and the cell line was named as CHO-12-5-12.

Figure 6:
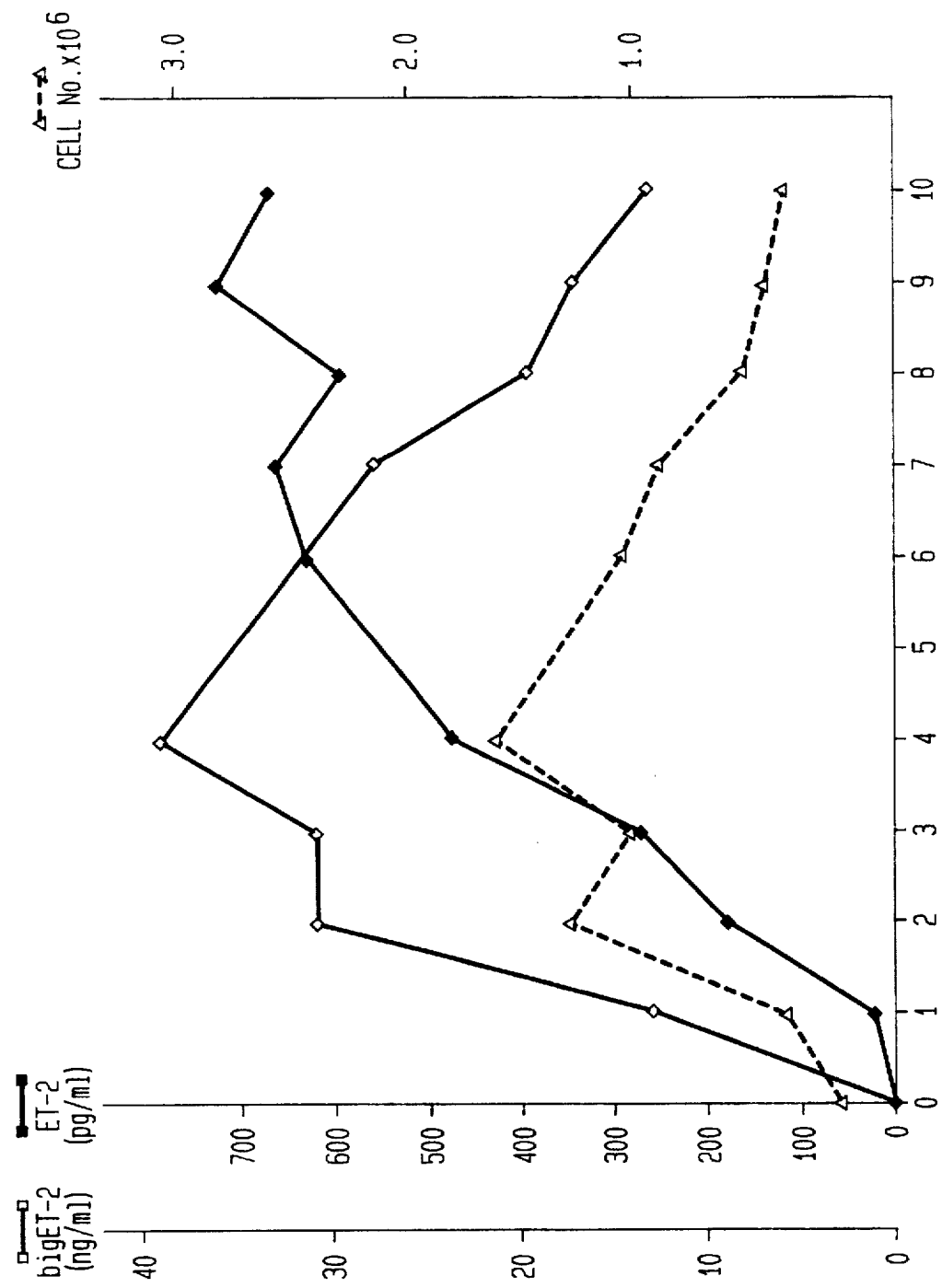
FIG. 6 is a graph relating to expression of human endothelin of the present invention.

The selected cells were cultured in DMEM medium containing 10% calf serum, and the immunoreactive ET of the culture solution was assayed. As a result, secretion of immunoreactive endothelin (closed squares) and big-endothelin (open squares) was observed, in addition to cell proliferation (open triangles show the total number of cells), as shown in FIG. 6.

EXAMPLE 6

Expression of Human Endothelin and Endothelin Precursor in CHO Cell Transformant and Determination of the Structures Thereof 1,500 ml of a culture supernatant of CHO-12-5-12 cells, CHO cells transformed with expression plasmid pTS612 into which the cDNA of human endothelin-2 was introduced, was divided into three portions, and each 500 ml portion was treated in the following manner.

Figure 7:
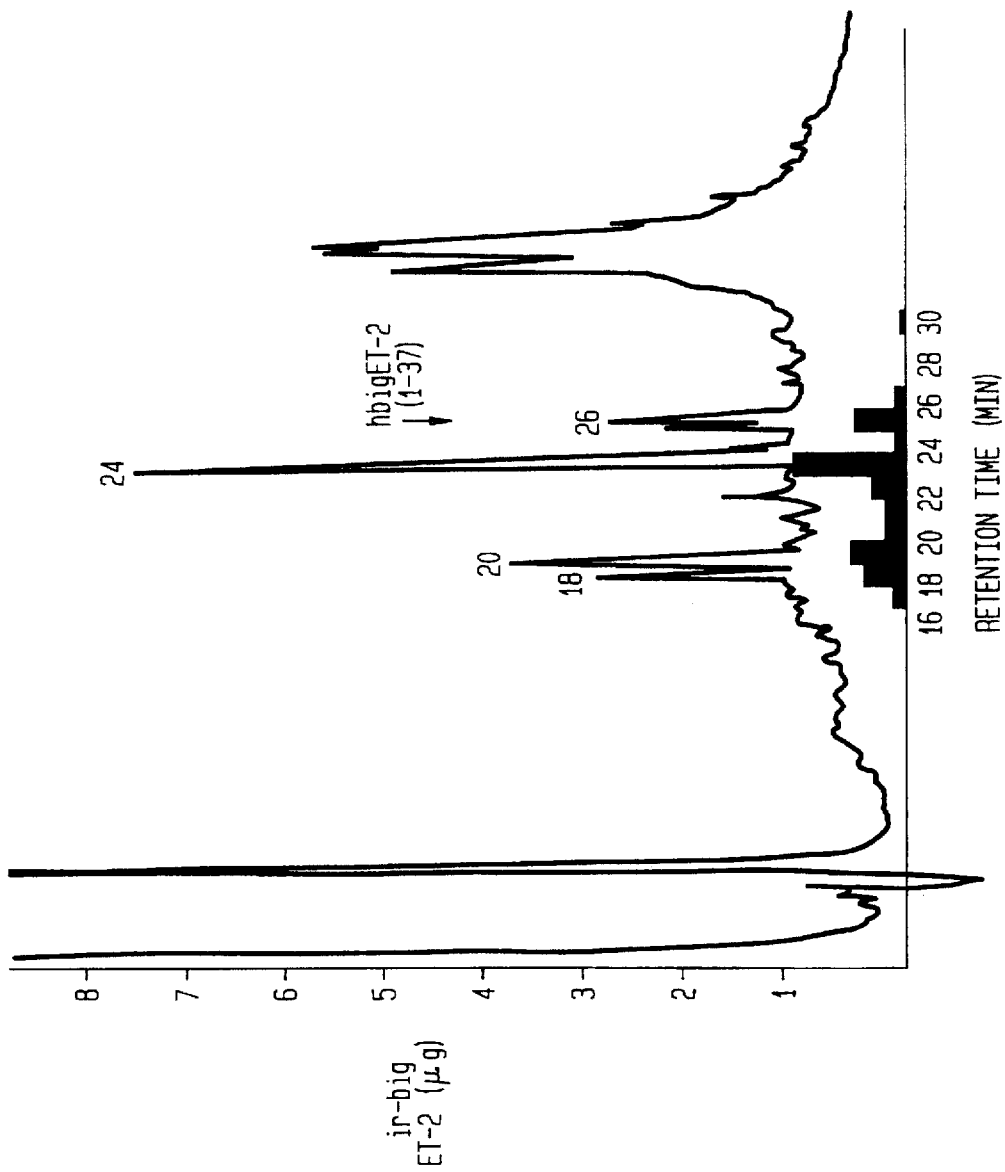
FIG. 7 is a reverse phase high performance chromatogram relating to expression of human endothelin-2 of the present invention and precursor thereof.

(1) Each portion was filtered through a 0.22-µm filter, and (2) subjected to AwETN40-affinity column chromatography (the way to prepare is described below). (3) The absorbed substances were separated by reverse phase high performance liquid chromatography (RP-HPLC) (FIG. 7). (4) Each of the resulting fractions was dried under vacuum, and (5) subjected to the enzyme immunoassay (EIA) of human big-endothelin-2 (1–37). (6) A fraction (peak 24 in FIG. 7) eluted 2 minutes before elution of synthesized human big-endothelin-2 (1–37) was taken, and (7) the amino acid sequence was determined with an AB1 (model 477A).

As a result, the sequence of 20 amino acid residues from the N-terminus was determined as Xaa-Ser-Xaa-Ser-Ser-Xaa-Leu-Asp-Lys-Glu-Xaa-Val-Tyr-Phe-Xaa-(His)-Leu-Asp-Ile-Ile-Xaa (SEQ ID NO:12).

The seventh Leu from the N-terminus apparently corresponded to Leu at the time that the nucleotide sequence of the cDNA of endothelin-2 was translated into the amino acid sequence. The N-terminus was deduced as Cys, and the above sequence was deduced as the sequence of endothelin-2, considering positions 1, 3, 11 and 15 of Cys.

Figure 8:
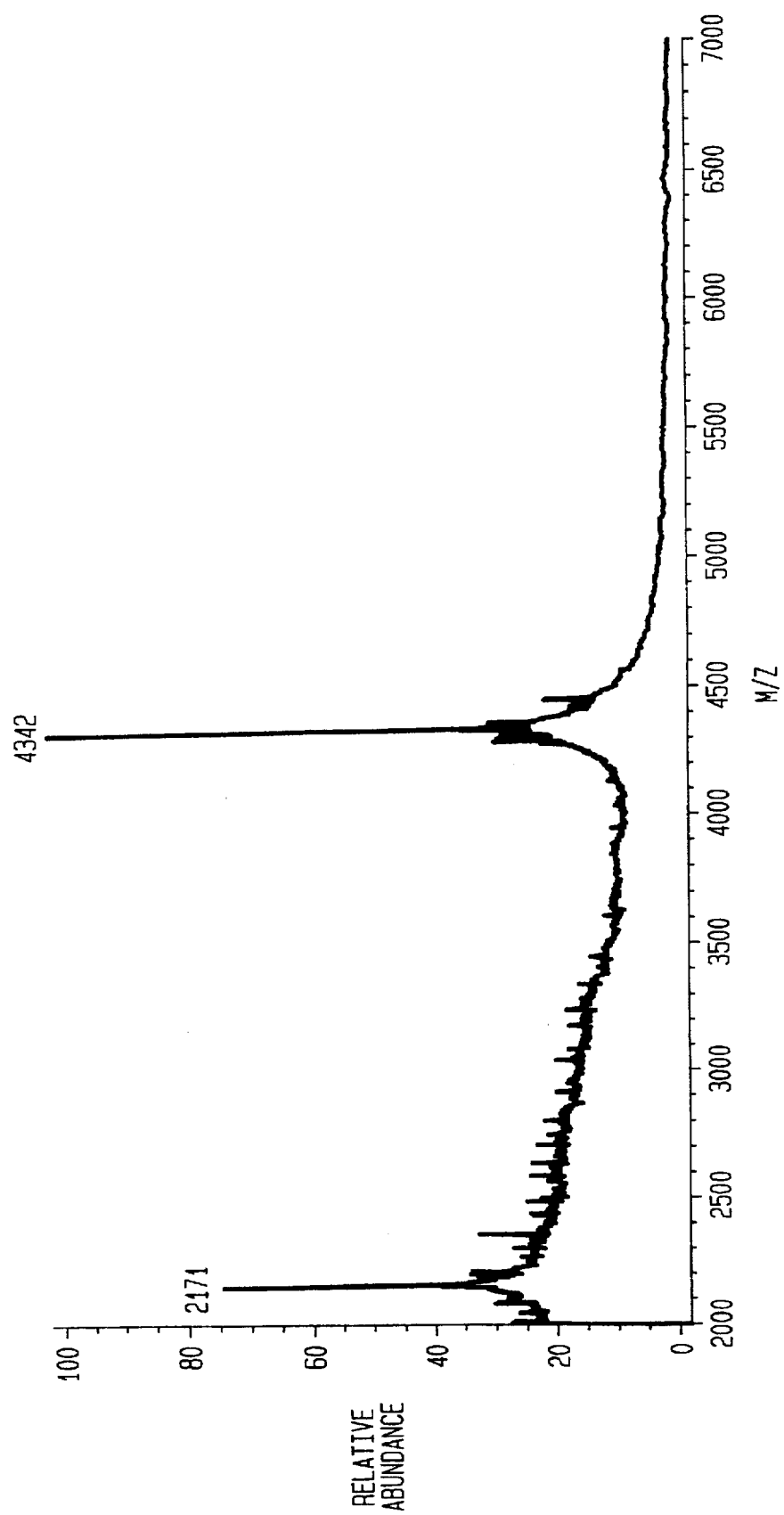
FIG. 8 is a mass spectrogram of human big endothelin-2 (1–38).

Although the N-terminal amino acid sequence of immunoreactive (ir)-big-endothelin-2 corresponding to peak 24 in FIG. 7 was shown above, the fraction of peak 24 was further analyzed with mass spectrographs (JMS-HX110HF and DA-500, JEOL) to determine the total molecular weight and the C-terminal amino acid sequence. As a result, the molecular weight was measured to be 4,342 (FIG. 8), and the following sequence consisting of 38 amino acid residues in which one Arg binds to the C-terminus of amino acids 1–37 based on the nucleotide sequence of the cDNA of human big-endothelin-2 (1–37) was deduced:

1
Cys Ser Cys Ser Ser Trp Leu Asp Lys Glu Cys Val Tyr Phe Cys

His Leu Asp Ile Ile Trp Val Asn Thr Pro Glu Gln Thr Ala Pro
38
Tyr Gly Leu Gly Asn Pro Pro Arg (SEQ ID NO:8)

This novel peptide is named human big-endothelin-2 (1–38). The molecule eluted at the same position as this human big-endothelin-2 (1–38) is presumed to exist also in human blood and a culture supernatant of human renal cancer cell ACHN, and this molecule as well as big-endothelin-2 (1–37) is a precursor of endothelin-2.

The antibody column using AwETN40 was produced by the following method.

AwETN40 antibodies were allowed to bind to a tresyl TOYOPAL (TOYO ROSHI Ltd. Japan) column according to methods known in the art. 500 ml of the culture supernatant of CHO-12-5-12 cells was treated with 1 ml of the obtained gel. Namely, a 1 cm diameter column was packed with the antibody-binding column to height of 0.5 cm. and a sample for RP-HPLC was prepared by the following steps:

(1) 8 ml of 0.05M glycine-HCl and 0.1M NaCl was allowed to flow.

(2) 30 ml of phosphate buffer was allowed to flow.

(3) 500 ml of the cell culture supernatant was allowed to flow.

(4) The column was washed with 30 ml of phosphate buffer.

(5) The column was washed with 10 ml of distilled water.

(6) Elution was conducted with 9 ml of 60% $CH_3CN$ and 0.1% TFA.

Then, the eluate was concentrated to 200 to 300 μl in the presence of $N_2$ gas, and subjected to RP-HPLC to obtain immunoreaction-positive substances, endothelin-2 and big-endothelin-2, by fractionation (FIG. 7).

The conditions of RP-HPLC were as follows:

Column: TSKgel ODS-80 (TOSO Ltd. Japan, 4.6 mm 1D×25 cm)

Eluent A: 5% $CH_3CN$, 0.05% TFA

Eluent B: 60% $CH_3CN$, 0.05% TFA

Elution was effected by a linear gradient of $CH_3CN$ from 18 to 60%. A portion of each fraction was taken and assayed by the EIA of human big endothelin-2 (1–37).

Thus, the endothelin precursor containing 21 amino acid residues of endothelin-2 (ET-2) was expressed in the CHO-K1 cell, an animal cell, and endothelin-2, big-endothelin-2 (big-ET-2)(1–37) and big-ET-2(1–38) larger in molecule than ET-2 and proteins having larger molecules were allowed to be secreted in the cell culture solution.

This system is useful to know the synthesis and secretion mechanisms of ET-2, and to develop methods for inhibiting the synthesis and secretion thereof. Further, this system is available for developing agents for inhibiting the synthesis of three kinds of endothelin peptides including peptides related to endothelin-1 and endothelin-3.

As described above, the cDNA coding for the precursor of human endothelin-2 was cloned, and the structure thereof was determined. This cDNA was introduced into the expression vector, whereby it became possible to express endothelin-2 and the precursor thereof.

Further, using the cDNA of human endothelin-2 as the probe, it became possible to elucidate the gene expression of endothelin-2 at the DNA level, along with endothelin-1 and endothelin-3 hitherto obtained by the present inventors. Furthermore, it became possible to diagnose diseases to which endothelin was related, in combination with the EIA of endothelin previously developed.

The following references, which are referred to for their disclosures at various points in this application, are incoporated herein by reference.

Proc. Natl. Acad. Sci. U.S.A. 79, 5485 (1982)
Proc. Natl. Acad. Sci. U.S.A. 81, 4577 (1984)
Amer. J. Physiol. 248, c550 (1985)
J. Cell Physiol. 132, 263 (1987)
J. Pharmacl. Exp. Ther. 236, 339 (1985)
Circulation Research 60, 422 (1987)
Japanese Patent Application No. 255381/1987
Japanese Patent Application No. 275613/1987
Japanese Patent Application No. 313155/1987
Japanese Patent Application No. 148158/1988
Japanese Patent Application No. 174935/1988
Japanese Patent Application No. 188083/1988
Japanese Patent Application No. 278497/1989
Japanese Patent Application No. 223389/1988
Japanese Patent Application No. 274990/1989
Proc. Natl. Acad. Sci. U.S.A. 86, 2863–2867 (1989)

We claim:

1. An isolated and purified precursor protein, which is represented by an amino acid sequence as defined in the Sequence Listing as SEQ ID NO:8.

2. An isolated and purified cDNA segment in which said cDNA segment is represented by the nucleotide sequence of Nos. 203 to 316 of SEQ ID NO:1.

3. A transformant carrying a DNA containing a cDNA segment coding for human endothelin-2 in which said cDNA segment coding for human endothelin-2 contains a nucleotide sequence represented by the nucleotide sequence of Nos. 203 to 316 of SEQ ID NO:1.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 1218 base pairs
( B ) TYPE: nucleic acid
( C ) STRANDEDNESS: double
( D ) TOPOLOGY: linear ( i i ) MOLECULE TYPE: cDNA to mRNA ( i x ) FEATURE:
( A ) NAME/KEY: CDS
( B ) LOCATION: 59..592

( x i ) SEQUENCE DESCRIPTION: SEQ ID NO:1:

```
AGGACGCTGG  CAACAGGCAC  TCCCTGCTCC  AGTCCAGCCT  GCGCGCTCCA  CCGCCGCT                  58

ATG  GTC  TCC  GTG  CCT  ACC  ACC  TGG  TGC  TCC  GTT  GCG  CTA  GCC  CTG  CTC        106
Met  Val  Ser  Val  Pro  Thr  Thr  Trp  Cys  Ser  Val  Ala  Leu  Ala  Leu  Leu
 1              5                        10                       15

GTG  GCC  CTG  CAT  GAA  GGG  AAG  GGC  CAG  GCT  GCT  GCC  ACC  CTG  GAG  CAG        154
Val  Ala  Leu  His  Glu  Gly  Lys  Gly  Gln  Ala  Ala  Ala  Thr  Leu  Glu  Gln
              20                       25                       30

CCA  GCG  TCC  TCA  TCT  CAT  GCC  CAA  GGC  ACC  CAC  CTT  CGG  CTT  CGC  CGT        202
```

```
Pro  Ala  Ser  Ser  Ser  His  Ala  Gln  Gly  Thr  His  Leu  Arg  Leu  Arg  Arg
          35                      40                          45

TGC  TCC  TGC  AGC  TCC  TGG  CTC  GAC  AAG  GAG  TGC  GTC  TAC  TTC  TGC  CAC      250
Cys  Ser  Cys  Ser  Ser  Trp  Leu  Asp  Lys  Glu  Cys  Val  Tyr  Phe  Cys  His
          50                      55                          60

TTG  GAC  ATC  ATC  TGG  GTG  AAC  ACT  CCT  GAA  CAG  ACA  GCT  CCT  TAC  GGC      298
Leu  Asp  Ile  Ile  Trp  Val  Asn  Thr  Pro  Glu  Gln  Thr  Ala  Pro  Tyr  Gly
65                       70                      75                          80

CTG  GGA  AAC  CCG  CCA  AGA  CGC  CGG  CGC  CGC  TCC  CTG  CCA  AGG  CGC  TGT      346
Leu  Gly  Asn  Pro  Pro  Arg  Arg  Arg  Arg  Arg  Ser  Leu  Pro  Arg  Arg  Cys
                    85                           90                    95

CAG  TGC  TCC  AGT  GCC  AGG  GAC  CCC  GCC  TGT  GCC  ACC  TTC  TGC  CTT  CGA      394
Gln  Cys  Ser  Ser  Ala  Arg  Asp  Pro  Ala  Cys  Ala  Thr  Phe  Cys  Leu  Arg
               100                      105                     110

AGG  CCC  TGG  ACT  GAA  GCC  GGG  GCA  GTC  CCA  AGC  CGG  AAG  TCC  CCT  GCA      442
Arg  Pro  Trp  Thr  Glu  Ala  Gly  Ala  Val  Pro  Ser  Arg  Lys  Ser  Pro  Ala
               115                     120                     125

GAC  GTG  TTC  CAG  ACT  GGC  AAG  ACA  GGG  GCC  ACT  ACA  GGA  GAG  CTT  CTC      490
Asp  Val  Phe  Gln  Thr  Gly  Lys  Thr  Gly  Ala  Thr  Thr  Gly  Glu  Leu  Leu
          130                     135                          140

CAA  AGG  CTG  AGG  GAC  ATT  TCC  ACA  GTC  AAG  AGC  CTC  TTT  GCC  AAG  CGA      538
Gln  Arg  Leu  Arg  Asp  Ile  Ser  Thr  Val  Lys  Ser  Leu  Phe  Ala  Lys  Arg
145                      150                     155                     160

CAA  CAG  GAG  GCC  ATG  CGG  GAG  CCT  CGG  TCC  ACA  CAT  TCC  AGG  TGG  AGG      586
Gln  Gln  Glu  Ala  Met  Arg  Glu  Pro  Arg  Ser  Thr  His  Ser  Arg  Trp  Arg
                    165                     170                     175

AAG  AGA  TAGTGTCGTG  AGCTGGAGGA  ACATTGGGAA  GGAAGCCCGC  GGGGAGAGAG              642
Lys  Arg

GAGGAGAGAA  GTGGCCAGGG  CTTGTGGACT  CTCTGCCTGC  TTCCTGGACC  GGGGCCTTGG              702

TCCCAGACAG  CTGGACCCAT  TTGCCAGGAT  TGGCACAAGC  TCCCTGGTGA  GGGAGCCTCG              762

TCCAAGGCAG  TTCTGTGTCC  TCGCACTGCC  CAGGGAAGCC  CTCGGCCTCC  AGACTGCGGA              822

GCAGCCTCCA  GTGCTGGCTG  CTGGCCCACA  GCTCTGCTGG  AAGAACTGCA  TGGGAGTAC               882

ATTCATCTGG  AGGCTGCGTC  CTGAGGAGTG  TCCTGTCTGC  TGGGCTACAA  ACCAGGAGCA              942

ACCGTGCAGC  CACGAACACG  CATGCCTCAG  CCAGCCCTGG  AGACTGGATG  GCTCCCCTGA             1002

GGCTGGCATC  CTGGCTGGCT  GTGTCCTCTC  CAGCTTTCCC  TCCCCAGAGT  TCTTGCACCC             1062

TCATTCCCTC  GGGACCCTCC  CAGTGAGAAG  GGCCTGCTCT  GCTTTCCTG   TCTGTATATA             1122

ACTTATTTGC  CCTAAGAACT  TTGAGAATCC  CAATTATTTA  TTTTAATGTA  TTTTTAGAC              1182

CCTCTATTTA  CCTGCGAACT  TGTGTTTATA  ATAAAT                                          1218
```

( 2 ) INFORMATION FOR SEQ ID NO:2:

( i ) SEQUENCE CHARACTERISTICS:
    ( A ) LENGTH: 178 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met  Val  Ser  Val  Pro  Thr  Thr  Trp  Cys  Ser  Val  Ala  Leu  Ala  Leu  Leu
1                   5                        10                          15

Val  Ala  Leu  His  Glu  Gly  Lys  Gly  Gln  Ala  Ala  Ala  Thr  Leu  Glu  Gln
               20                      25                      30

Pro  Ala  Ser  Ser  Ser  His  Ala  Gln  Gly  Thr  His  Leu  Arg  Leu  Arg  Arg
               35                      40                      45

Cys  Ser  Cys  Ser  Ser  Trp  Leu  Asp  Lys  Glu  Cys  Val  Tyr  Phe  Cys  His
```

|           | 50            |               |               | 55            |               |               | 60            |               |               |
|-----------|---------------|---------------|---------------|---------------|---------------|---------------|---------------|---------------|---------------|

Leu Asp Ile Ile Trp Val Asn Thr Pro Glu Gln Thr Ala Pro Tyr Gly
65                  70                  75                  80

Leu Gly Asn Pro Pro Arg Arg Arg Arg Arg Ser Leu Pro Arg Arg Cys
                85                  90                  95

Gln Cys Ser Ser Ala Arg Asp Pro Ala Cys Ala Thr Phe Cys Leu Arg
            100                 105                 110

Arg Pro Trp Thr Glu Ala Gly Ala Val Pro Ser Arg Lys Ser Pro Ala
            115                 120                 125

Asp Val Phe Gln Thr Gly Lys Thr Gly Ala Thr Thr Gly Glu Leu Leu
            130                 135                 140

Gln Arg Leu Arg Asp Ile Ser Thr Val Lys Ser Leu Phe Ala Lys Arg
145                 150                 155                 160

Gln Gln Glu Ala Met Arg Glu Pro Arg Ser Thr His Ser Arg Trp Arg
                165                 170                 175

Lys Arg ( 2 ) INFORMATION FOR SEQ ID NO:3:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Cys Ser Cys Ser Ser Leu Met Asp Lys Glu Cys Val Tyr Phe Cys His
1               5                   10                  15

Leu Asp Ile Ile Trp
            20

( 2 ) INFORMATION FOR SEQ ID NO:4:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Cys Ser Cys Ser Ser Trp Leu Asp Lys Glu Cys Val Tyr Phe Cys His
1               5                   10                  15

Leu Asp Ile Ile Trp
            20

( 2 ) INFORMATION FOR SEQ ID NO:5:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Cys Ser Cys Asn Ser Trp Leu Asp Lys Glu Cys Val Tyr Phe Cys His
1               5                   10                  15

Leu Asp Ile Ile Trp
            20

( 2 ) INFORMATION FOR SEQ ID NO:6:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:6:

```
Cys Thr Cys Phe Thr Tyr Lys Asp Lys Glu Cys Val Tyr Tyr Cys His
1               5                   10                  15

Leu Asp Ile Ile Trp
            20
```

( 2 ) INFORMATION FOR SEQ ID NO:7:

( i ) SEQUENCE CHARACTERISTICS:
      ( A ) LENGTH: 37 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:7:

```
Cys Ser Cys Ser Ser Trp Leu Asp Lys Glu Cys Val Tyr Phe Cys His
1               5                   10                  15

Leu Asp Ile Ile Trp Val Asn Thr Pro Glu Gln Thr Ala Pro Tyr Gly
            20                  25                  30

Leu Gly Asn Pro Pro
            35
```

( 2 ) INFORMATION FOR SEQ ID NO:8:

( i ) SEQUENCE CHARACTERISTICS:
      ( A ) LENGTH: 38 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:8:

```
Cys Ser Cys Ser Ser Trp Leu Asp Lys Glu Cys Val Tyr Phe Cys His
1               5                   10                  15

Leu Asp Ile Ile Trp Val Asn Thr Pro Glu Gln Thr Ala Pro Tyr Gly
            20                  25                  30

Leu Gly Asn Pro Pro Arg
            35
```

( 2 ) INFORMATION FOR SEQ ID NO:9:

( i ) SEQUENCE CHARACTERISTICS:
      ( A ) LENGTH: 99 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:9:

```
CATGCCCAAG GCACCCACCT TCGGCTTCGC CGTTGCTCCT GCAGCTCCTG GCTCGACAAG    60
GAGTGCGTCT ACTTCTGCCA CTTGGACATC ATCTGGGTG                           99
```

( 2 ) INFORMATION FOR SEQ ID NO:10:

( i ) SEQUENCE CHARACTERISTICS:

(A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:10:

GGTGGCGACG ACTCCTGGAG CCCG 24

(2) INFORMATION FOR SEQ ID NO:11:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:11:

TTGACACCAG ACCAACTGGT AATG 24

(2) INFORMATION FOR SEQ ID NO:12:

(i) SEQUENCE CHARACTERISTICS:
            (A) LENGTH: 21 amino acids
            (B) TYPE: amino acid
            (D) TOPOLOGY: linear (ii) MOLECULE TYPE: peptide (xi) SEQUENCE DESCRIPTION: SEQ ID NO:12:

Xaa  Ser  Xaa  Ser  Ser  Xaa  Leu  Asp  Lys  Glu  Xaa  Val  Tyr  Phe  Xaa  His
    1                   5                        10                       15

Leu  Asp  Ile  Ile  Xaa
                    20